US007807188B2

(12) United States Patent
Hoath et al.

(10) Patent No.: US 7,807,188 B2
(45) Date of Patent: Oct. 5, 2010

(54) SIMULATED VERNIX COMPOSITIONS FOR SKIN CLEANSING AND OTHER APPLICATIONS

(75) Inventors: Steven B. Hoath, Cincinnati, OH (US); William L. Pickens, Cincinnati, OH (US); Martha O. Visscher, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 662 days.

(21) Appl. No.: 10/512,933

(22) PCT Filed: May 2, 2003

(86) PCT No.: PCT/US03/13612

§ 371 (c)(1),
(2), (4) Date: May 10, 2005

(87) PCT Pub. No.: WO03/092646

PCT Pub. Date: Nov. 13, 2003

(65) Prior Publication Data

US 2005/0232890 A1    Oct. 20, 2005

Related U.S. Application Data

(60) Provisional application No. 60/377,430, filed on May 3, 2002, provisional application No. 60/439,966, filed on Jan. 14, 2003.

(51) Int. Cl.
*A61K 9/00* (2006.01)
(52) U.S. Cl. .................... 424/401; 424/400; 424/450
(58) Field of Classification Search ....................... None
See application file for complete search history.

(56) References Cited

U.S. PATENT DOCUMENTS

| 5,753,259 A | * | 5/1998 | Engstrom et al. | .............. 424/50 |
| 6,333,041 B1 | * | 12/2001 | Hoath et al. | ................ 424/401 |
| 2003/0077307 A1 | * | 4/2003 | Klofta et al. | ................ 424/401 |

FOREIGN PATENT DOCUMENTS

WO    WO99/44583    *    9/1999

(Continued)

OTHER PUBLICATIONS

Youssef, et al. "Surface free energy characterization of vernix caseosa. Potential role in waterproofing the newborn infant." Skin Research and Technology 2001; 7: 10-17.*

(Continued)

*Primary Examiner*—Robert A Wax
*Assistant Examiner*—Melissa S Mercier
(74) *Attorney, Agent, or Firm*—Thompson Hine LLP

(57) ABSTRACT

A composition and a method of producing a composition which simulates hydration, cleansing and other properties of native vernix. The composition contains hydrated synthetic cells in a lipid matrix to provide rheological properties which are substantially similar to those of native vernix, and may also contain proteins. In one embodiment, the composition contains cubosomes/water with up to 30% protein and about 5% lipid to about 30% lipid. The composition may be used to cleanse newborn skin, compromised skin surfaces, as well as normal skin, to provide hydration/barrier function, and other applications.

11 Claims, 10 Drawing Sheets

FOREIGN PATENT DOCUMENTS

WO          WO9944582     *    9/1999

OTHER PUBLICATIONS

Youssef, Wael, Surface Free Energy characterization of vernix caseosa. Potential role in waterproofing the newborn infant, 2001, Skin Research and Technology, pp. 10-17.*

Youssef, Wael, Surface free energy characterization of vernix caseosa. Potential role in waterproofing the newborn infant, 2001, Skin research and technology, 7, 10-17.*

Youseff et al. "Surface free energy chracterization of vernix caseosa, Potential role in waterproffing the newborn infant" Skin Research and Technology 2001:7:10-17.*

* cited by examiner

CLEANSING EXPERIMENT

AQUAPHOR BEFORE SOILING

AQUAPHOR AFTER CLEANSING

CLEANSING EXPERIMENT

JOHNSON AND JOHNSON BABY WASH BEFORE SOILING

JOHNSON AND JOHNSON BABY WASH AFTER CLEANSING

CLEANSING EXPERIMENT

PONDS COLD CREAM BEFORE SOILING

PONDS COLD CREAM AFTER CLEANSING

SIMULATED VERNIX COMPOSITIONS FOR SKIN CLEANSING AND OTHER APPLICATIONS

RELATED APPLICATIONS

This application claims priority from U.S. Provisional application Ser. No. 60/377,430 filed May 3, 2002 and U.S. Provisional application Ser. No. 60/439,966 filed Jan. 14, 2003.

FIELD OF THE INVENTION

A composition simulating natural vernix and uses for the composition.

BACKGROUND OF THE INVENTION

Vernix caseosa (vernix) is a lipid-rich naturally occurring skin protectant composed of sebum, epidermal lipids, and desquamated epithelial cells. It covers the skin of the developing fetus in utero while the fetus is completely surrounded by amniotic fluid. Vernix consists of hydrated cells dispersed in a lipid matrix. Natural vernix comprises about a 10% lipid fraction by weight, about a 10% protein fraction by weight, and about an 80% volatile fraction by weight. The lipid matrix undergoes a transition to a more fluid form at physiological temperatures and with the application of shear forces, such as those encountered with movement. Vernix is a covering for the skin of the fetus that resembles the stratum corneum except that it lacks multiple rigid desmosomal connections. Consequently, vernix exhibits a viscous fluid character.

The lipid component of vernix has been reported in *J. Invest. Dermatol.* 78:291(1982); *Lipids* 6:901(1972); *J. Clin. & Lab. Investigation* 13:70 (1961); *J. Invest. Dermatol.*, 44:333 (1965); and U.S. Pat. No. 5,631,012, each of which is incorporated by reference herein in its entirety. Lipids, defined herein as fats or fat-like substances, include lecithin and other phospholipids, squalene, waxes, wax esters, sterol esters, diol esters, triglycerides, ceramides in which the fatty acid components may be one or more of the following: α-hydroxy 6-hydroxy-4-sphingenine, α-hydroxy phytosphingosine, α-hydroxy sphingosine, ester linked ω-hydroxy 6-hydroxy-4-sphingenine, non-hydroxy phytosphingosine, non-hydroxy sphingosine, and/or ester linked ω-hydroxysphingosine; free sterols, and four classes of fatty acids ranging in chain length from $C_{12}$ to $C_{26}$, (straight chain saturated, straight chain unsaturated, branched chain saturated, and branched chain unsaturated). The lipid fraction may contain, with the relative percentages indicated, squalene (9%), ceramides (10%) aliphatic waxes (12%), sterol esters (33%), diesters (7%), triglycerides (26%), free sterols (9%), and other lipids (4%). The fatty acids within the aliphatic waxes may be branched and the branched fatty acids may be methylated.

Because of its anticipated skin maturation and protectant properties, vernix appears to have promise as a clinically effective therapeutic agent. Application of vernix to clinical use, however, has been limited by the difficulty in obtaining samples of sufficient volume, the possibility of disease transmission, and the physical properties of native vernix.

Regarding its physical properties, vernix in utero is a tractable semi-solid, whereas vernix ex utero is a nonhomogeneous intractable compound with a consistency comparable to cheese or hardened cake frosting. Vernix is not completely soluble in conventional solvents such as absolute ethanol, 95% ethanol, 2-propanol, and combinations of chloroform and methanol. Thus, controlled and uniform administration of vernix to a surface is difficult. It has been reported that the surfactant polysorbate 80 (Tween 80) may solubilize vernix, but Tween 80 is toxic to living cells and therefore cannot be used clinically. Isolated reports disclose vernix directly scraped from a newborn for smearing over wounds (SU Patent No. 1718947A) or an artificial lipid composition as a cosmetic moisturizer (U.S. Pat. No. 5,631,012).

Natural vernix contains proteins which, in general, are multi-determinant antigens. Thus, the protein component of vernix may be capable of inducing an immune response and reacting with the products of an immune response. Proteins with a greater degree of complexity generally provoke a more vigorous immune response.

The protein fraction of natural vernix consists of epidermally derived proteins, primarily keratin and filaggrin, trace amounts (micromolar to millimolar concentrations) of regulatory proteins such as epidermal growth factor, and trace amounts (nanomolar to micromolar concentrations) of surfactant protein such as surfactant associated protein-A and surfactant associated protein-B.

Because virtually all proteins are immunogenic in an appropriate individual, and because of the different type and complexity of proteins in natural vernix, at least some immune response would be anticipated when vernix is applied to non-self (other than the baby and/or the mother). The response encompasses physical, biochemical, and molecular changes, such as stimulation of T cells, B cells, and macrophages, hypersensitivity reactions or allergic reactions, inflammation, fever, etc.

We have previously reported that synthetic vernix may be produced by mixing one part of natural vernix, removed from the infant at the time of delivery, with any of the following components in the proportions indicated: either about 0.005 to about 0.05 parts phospholipid, or trace amounts of about nanomolar to micromolar concentrations of pulmonary surfactant proteins such as surfactant A and/or surfactant B, or 5 parts dimethylsulfoxide (DMSO), or 1 part amniotic fluid, or combinations of the above. Alternatively, synthetic vernix may also be produced by combining lipids to comprise about a 10% fraction of the entire volume, proteins to comprise about a 10% fraction of the entire volume, and water to comprise the remaining about 80% of the entire volume. The following lipid components are combined in the relative percentages indicated: squalene (9%), aliphatic waxes (12%), sterol esters (33%), diesters (7%), triglycerides (26%), free sterols (9%), and other lipids (4%). The fatty acids within the waxes may be branched and the branched fatty acids may be methylated. The protein components, combined to constitute about a 10% fraction, are epidermally derived proteins, primarily keratin and filaggrin, with trace amounts of about micromolar to millimolar concentrations of regulatory proteins such as epidermal growth factor, and trace amounts of about nanomolar to micromolar concentrations of surfactant protein such as surfactant A and surfactant B.

Skin cleansing formulations generally contain surfactants that emulsify soils on the skin surface for removal with a water rinse. Surfactants may be anionic, cationic, nonionic, or zwitterionic and can be in the form of a bar, a liquid, a cream, a gel, etc. Surfactants vary markedly in their effects on the skin and differ significantly in their inherent irritancy to skin. They have been shown to vary in their effects on corneocyte swelling, disaggregation, and damage. Surfactants, as well as other topical treatments, can vary greatly in their effects on the permeability barrier of skin. For example, the effects of sodium dodecyl sulfate (SDS) and acetone on human skin in vivo (biopsy specimens) were evaluated by electron microscopy. Damage to nucleated epidermal cells and disruption of lipid extrusion were observed for skin treated with 0.5% SDS, even though the upper stratum corneum was intact. Acetone treatment resulted in disruption of epidermal lipid lamellae and loss of lamellar cohesion throughout the stratum corneum.

The amount of residual material left on the skin surface after cleansing depends upon properties of the surfactant, including its interaction with calcium and magnesium in the rinse water. The amount of surfactant used in cleansing and the extent of surfactant dilution with rinsing (i.e., volume of rinse water) can impact the residual material remaining on the skin surface. Procedures for bathing newborns frequently involve minimal rinsing to minimize the cooling effects of full body water exposure. Consequently, due to the low volume and short duration of rinsing, the level of residual surfactant on newborn skin is expected to be high.

Given the irritating and drying effects of surfactants on skin, the advisability of bathing infants with cleansing products warrants re-evaluation. It has been recommended to use mild cleansers with few ingredients to minimize irritant and allergic dermatoses in infants, and to use specialized preparations for specific dermatoses that might occur (*J Eur Acad Dermatol Venereol* 2001;15,12). One of the functions of bathing a newborn is to remove blood and pathogens to prevent transmission to others. A study compared the pathogen colonization rate for a group of 62 infants bathed using a mild cleanser, with the colonization rate for a group of 65 infants bathed with water alone (*Birth* 2001;28,161). Colonization of the skin increased over time in both groups, with no difference in type or quantity of microorganisms. These data indicate that the cleanser does not impact bacterial colonization.

Various cleansing treatments on the skin of infants aged 2 weeks to 16 months were evaluated (*Dermatology* 1997;195, 258). Parallel treatment groups of 7-10 infants were washed one time with water alone, a synthetic liquid cleanser, a synthetic bar cleanser, or a fatty acid soap. Measures of skin pH, hydration, and surface lipid content were made before and ten minutes after washing. All four treatments increased the skin pH over its starting pH, with water alone resulting in the smallest pH increase and soap resulting in the largest pH increase. All three cleansers resulted in a significantly greater pH increase than water alone, with the fatty acid soap significantly greater than the synthetic liquid or bar cleanser. The authors indicated that the tap water used in bathing was alkaline (pH 7.8-8.2), but the extraction of water-soluble amino acids in natural moisturizing factor due to bathing is expected to give rise to a higher pH. No differences were detected in skin hydration, either as a result of bathing or the cleansing product. This finding is inconsistent with the results of another study reporting decreased hydration following bathing, but in the latter study, the time after bathing was shorter (10 min versus 15 min), the base sizes of the infants were smaller, and the age ranges differed (3-6 months versus 2 weeks-16 months) (*Ped Dermatol* 2002;19,473). In another study determining the effects of bathing a group of infants over a two week period with a whey-based product, decreased hydration, pH and erythema were reported, but the changes were not statistically significant (*Schweiz Rundsch Med Prax* 1998;87,617).

The effects of water and surfactants can be further exacerbated by pre-existing skin conditions or other environmental factors. The effects of washing with a cleanser on stratum corneum and epidermal thickness were evaluated among normal and atopic (having allergic reactions, e.g., hay fever, asthma, atopic dermatitis) subjects. Soaps decreased the number of cell layers in the atopic subjects but not the normal subjects, suggesting that atopic individuals have increased susceptibility to cleansers.

The combination of washing with surfactants and decreased environmental humidity has also been investigated. In human adults, the effects of irritant dermatitis due to repeated water and/or surfactant exposure were exacerbated at decreased absolute humidity. Animals exposed to low humidity for a short time (two days) exhibited increased epidermal proliferation following surfactant (SDS) exposure, compared to animals housed at normal or high humidity. Additionally, animals exposed to high humidity for two weeks had greater epidermal proliferation after exposure to surfactant than did animals exposed to low or normal humidity for two weeks. This suggests that the effects of water and surfactants may be greater under humidity extremes in either infants or neonates.

Skin of premature neonates has poor epidermal barrier properties and increased susceptibility to damage. These factors, coupled with the overall medical instability of premature infants, must be balanced with the need for practices, such as bathing, to reduce the risk of infection. One study investigated the effects of reduced bathing frequency (once in four days compared to once a day) on skin pathogen colonization among a group of premature infants. No differences were found in skin flora on days 2, 3, or 4 after bathing (*J Obstet Gynecol Neonatal Nurs* 2000;29,584). Reduced bathing frequency for premature infants has been, and continues to be, recommended as a general standard of care in the neonatal nursery (*J Obstet Gynecol Neonatal Nurs* 1999;28,241). The specific effects of bathing on preterm infant physiology and behavior were investigated in a group of ten subjects, with responses measured ten minutes before, during, and ten minutes after the bath. Significant increases were observed for heart rate, cardiac oxygen demand, and motor behavior, accompanied by a significant decrease in oxygen saturation.

Compared to term infants, preterm infants are more susceptible to transdermal exposures due to their immature epidermal barrier. At one time, cleansing products containing 3% hexachlorophene were regularly used for full body bathing of premature neonates, but subsequent evaluations of the neurotoxic effects indicated that vacuolar encephalopathy was related to hexachlorophene exposure. The use of hexachlorophene-containing products was therefore discontinued for this population. Alternatives were proposed through testing on the control of pathogenic bacteria, and included Lactacyd (an alkyl sulfate surfactant) and Hibitane (chlorhexidine). Subsequent evaluation of Lactacyd, however, showed that it increased transepidermal water loss (TEWL) and was inappropriate for premature infants, and chlorhexidine was found to be cytotoxic to fibroblasts and keratinocytes in culture and therefore contraindicated for preterm infants.

Thus, the use of topical products on premature infant skin, including surfactants, cleansers, antiseptics, etc., must be carefully considered. Factors which govern the relative effect on the infant include stratum corneum thickness and integrity, amount of surface residue, inherent irritantcy of residual materials, and partition coefficient through the stratum corneum. While the stratum corneum of preterm infants develops rapidly after birth under the influence of the relatively dry environmental condition, the barrier function is not fully competent for several weeks after birth and is more permeable to exogenous materials. In particular, bathing involves minimal rinsing of the skin surface, and thus residual materials remain on the skin surface.

Stratum corneum, the outermost surface of the skin, continually self-cleanses through the process of desquamation. In utero, during the third trimester, vernix gradually detaches from the fetal skin under the influence of mechanical stress and pulmonary surfactant, yielding turbid amniotic fluid. At birth, residual vernix on the skin surface forms the physical interface between the newborn infant and a nonsterile environment Most surfactants used in commercially available cleansing products interact with and alter the epidermal barrier, as evidenced by numerous studies using in vivo systems. A consideration of the response of infant skin, versus adult skin, to topically applied treatments is useful in order to determine the potential effects of topical treatments in the preterm infant. For example, the infant has a greater surface area to body weight ratio and absorbs proportionately greater quantities than adults. Tissue distribution depends on age, and tissue affinity may vary between infants and adults, leading to different overall effects.

There is, therefore, a need to determine methods and compositions that are useful in compromised skin, such as that found in a preterm infant having immature epidermal barrier structure and function, as well as normal skin.

SUMMARY OF THE INVENTION

One embodiment of the invention is a simulated vernix composition of hydrated synthetic cells (e.g., cubosomes, polymersomes, colloidosomes) dispersed in a lipid matrix. Another embodiment is a simulated vernix composition containing hydrated synthetic cells and proteins (e.g., keratin, filaggrin, epidermal growth factor, surfactant associated protein-A, -B, -D, the peptide natural moisturizing factor) dispersed in a lipid matrix. The lipid matrix may contain cholesterol, cholesterol esters, ceramides, triglycerides, fatty acids, phospholipids, wax esters, wax diesters, and/or squalene. The lipids constitute about 5 wt % to about 30 wt % of the total composition. The protein, if present, constitutes about 0.1 wt % to about 30 wt % of the total composition.

Another embodiment is a method of treating skin by applying a physiologically compatible composition containing hydrated synthetic cells in a lipid matrix in an amount effective to treat skin. It may be applied to intact or compromised skin, for example, to bring about skin growth, maturation, or healing when applied to a wound or ulcer, or to provide a barrier, such as a water repellent or moisturizing function, when applied to normal, chapped, or irritated skin.

Another embodiment is an apparatus that contains a device for contacting a skin surface (e.g., a pad, bandage, diaper, dressing, etc.) which carries a pharmaceutical composition comprising hydrated synthetic cells in a lipid matrix.

Other embodiments are compositions and methods of treating skin by providing a physiologically compatible composition containing hydrated synthetic cells in a lipid matrix in an amount sufficient such that the composition applied to the skin surface provides various physical properties, such as a minimum surface free energy of about 20 dynes/cm; a contact angle with benzyl alcohol in the range of about 18.0 to about 24.7, a contact angle with diiodomethane in the range of about 30.0 to about 38.3, a contact angle with glycerol in the range of about 71.9 to about 76.5, and a contact angle with water in the range of about 82.7 to about 84.3; a critical surface tension in the range of about 38 dynes/cm to about 41 dynes/cm; a critical surface tension in the range of about 38 dynes/cm to about 41 dynes/cm; a critical surface tension greater than 36 dynes/cm; or an amount sufficient to effect barrier repair as a semipermeable film.

Another embodiment is a method of using a either natural or synthetic vernix, or a simulated vernix composition, to remove soil from a skin surface. The composition is applied to the soiled surface, then is removed along with the soiling material. The method may be used on a premature or full term infant, a child, an adult, a geriatric patient, and the composition may be used on an intact or compromised surface, such as a wound or ulcer. The method may be used with a vernix composition that also contains a soap and/or surfactant.

Another embodiment is a method for fully or partially cleansing a baby (full term or premature) immediately after birth with a composition containing isolated vernix to remove amniotic fluid, endogenous vernix, meconium, blood and other fluids, upon removing the composition.

Another embodiment is a method of cleaning a soiled skin surface by applying a composition consisting essentially of isolated physiologically compatible vernix under conditions to emulsify the soiling material in the vernix, and then removing the vernix and emulsified soiling material. The amount of vernix may be up to about 16 mg/cm$^2$.

Another embodiment is a method of cleansing skin by applying a nontoxic film having a thickness up to about 16 mg/cm$^2$ and consisting essentially of isolated physiologically compatible vernix to a layer of epithelial cells to provide a skin cleansing effect. The film may be applied either directly or indirectly to the surface; for example, it may be applied to a wash cloth, a wipe, a bandage, a pad, etc. Another embodiment is a method of cleansing an epithelial layer by applying a non-toxic film having a thickness of up to about 16 mg/cm$^2$ and consisting essentially of isolated physiologically compatible vernix to the epithelial layer, and then removing the film from the cleansed tissue.

Another embodiment is a method to protect a skin surface of an individual who is, or may be, susceptible to commercially available cleansing products (e.g., one allergic to some commercial soaps or cleansers). In the method, a composition consisting essentially of isolated physiologically compatible vernix is applied to a skin surface of this individual in an amount up to 16 mg/cm$^2$ before exposing the skin surface to the product.

Another embodiment is a method to remove a soiling material from a skin surface by providing isolated physiologically compatible vernix and at least one soap or surfactant to the soiled surface under conditions resulting in flocculation and detachment of the soil from the surface.

The invention will be further appreciated with respect to the following detailed description, figures, and examples.

DETAILED DESCRIPTION

Figure 1C:
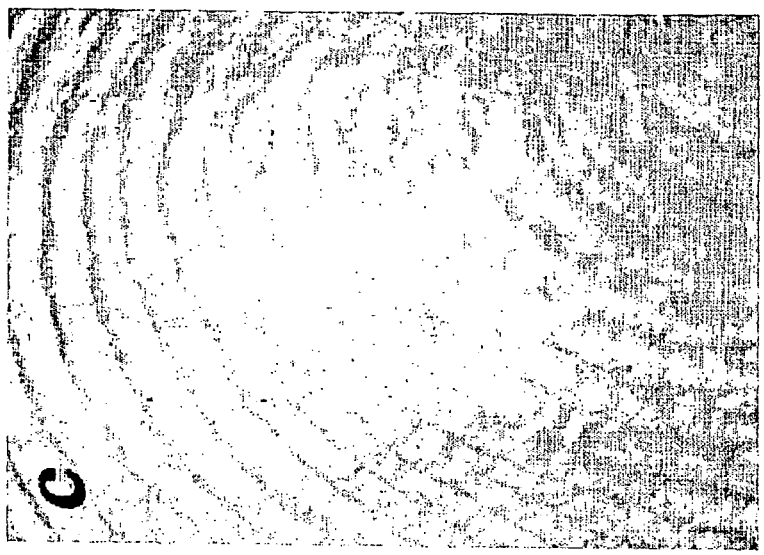
FIGS. 1A, 1B, and 1C are digital images of hand skin, either unsoiled (FIG. 1A), after application of a soiling material (FIG. 1B), or after application of vernix to the soiled area (FIG. 1C).

A nontoxic simulated vernix composition contains a component of simulated cells and a component of at least one lipid. In one embodiment, the composition contains a component of at least one protein. This composition provides the barrier and hydration functions of natural vernix, but reduces or eliminates an immune response.

Native vernix, as used herein, encompasses vernix as it is obtained from a newborn, as well as vernix obtained from a newborn that has been rendered tractable, as described in U.S. Pat. Nos. 5,989,577; 6,113,932; 6,333,041; and U.S. patent application Ser. Nos. 09/850,844; 10/241,184; and 60/377,430, each of which is expressly incorporated by reference herein in its entirety. An immune response, as used herein, is defined as immune system-provoked physical, biochemical, and/or molecular changes such as occurs in an individual challenged with a non-self protein, whether the symptoms of such a response are subclinical or clinical. A reduced immune response, as used herein, is any alleviation or diminution in kind, extent, duration, severity, etc. of the immune response. A protein, as used herein, also encompasses peptides and individual amino acids.

In the inventive composition, the cell component of native vernix is replaced by synthetic structures which perform the hydration functions of cells; these structures may be termed "simulated cells" or "synthetic cells". The simulated cells in small particle form are mixed into a lipid matrix. The lipid matrix contains at least one commercially available lipid that is present in native vernix The water soluble protein component is in a water phase that is bicontinuous with the simulated cell component. In embodiments where a protein component is present, it serves the role of the protein-based natural cells in native vernix. The protein component may be commercially available proteins, recombinant protein, synthetic proteins, etc. Proteins may be one or more of keratin, filaggrin, epidermal growth factor, surfactant associated proteins A, B, and/or D, and the peptide natural moisturizing factor (NMF). Hyaluronic acid may also be included. Proteins may be epidermally derived from a source other than native vernix.

Simulated cells are dispersed in a matrix of at least one lipid. Any or all of the following lipids may be used, each of which is found in native vernix in the concentration indicated, and each of which is available commercially (for example, Sigma, St. Louis Mo.): cholesterol esters, ceramides, triglycerides, cholesterol free fatty acids, phospholipids, wax esters, squalene, wax diesters, and cholesterol sulfate.

In one embodiment, the lipid component of simulated vernix is in the range of about 5% to about 30%, and the protein component of simulated vernix is in the range of about 5% to about 30%, with the simulated cell/water component constituting the remaining concentration. In another embodiment, the lipid component is in the range of about 5% to about 30%, and the protein component may be up to about 30%. The absolute concentrations of lipid and protein components may vary, such that water is released slowly and maintains hydration by picking up moisture. The concentration of one or more of the lipid components is generally in the ranges shown to provide the 5%-30% lipid component of the simulated vernix, although the exact concentration is not critical:

| | |
|---|---|
| cholesterol esters | about 20% to about 35% |
| ceramide | about 10% to about 20% |
| triglycerides | about 10% to about 20% |
| cholesterol | about 5% to about 10% |
| free fatty acids | about 5% to about 10% |
| phospholipids | about 5% to about 10% |
| wax esters | about 2% to about 8% |
| squalene | about 0.5% to about 5% |
| wax diesters | about 0.5% to about 6% |
| cholesterol sulfate | about 0.1% to about 3% |

The composition of the lipid phase may be varied to provide the desired spreading characteristics and viscosity for the final composition. For example, a relatively higher wax content will produce a less spreadable, more viscous composition than a relatively lower wax content; a relatively higher free fatty acid and/or triglyceride content will produce a more easily spreadable, less viscous composition than a relatively lower free fatty acid and/or triglyceride content.

The protein component of natural vernix is provided by one or more protein from a source other than native vernix. For example, proteins may be synthesized using standard synthesis techniques known to one skilled in the art. Proteins may also be made by recombinant molecular techniques known to one skilled in the art. Proteins may also be obtained from commercial sources, for example Sigma (St. Louis Mo.). Thus, the protein component of the inventive composition may be from any source other than native vernix; the protein component may in fact contain one or more proteins from a natural source. As one example, cultured mammalian cells other than those derived from vernix may be used as a source of the protein component. As another example, non-human non-animal cellular materials may be used as a source of the protein component As another example, surfactant protein D may be obtained from cow lung and used as a source of the protein component. As another example, keratins may be extracted from animal and human hair, wool, etc. and used as a source of the protein component.

In the inventive composition, the cellular component of native vernix is replaced with a component which mimics cells in performing a function of cells in native vernix. The "cellular" component, also referred to herein as simulated cells, hydrates a surface to which the inventive composition is applied. It does this by slowly releasing water and by transporting water vapor, as cells do in native vernix. The composition may endogenously perform this hydration function, or the composition may be engineered, modified, etc. to perform this hydration function. To replace the cellular component of natural vernix, any dispersed particle that is capable of controllably retaining and releasing water in a lipid environment may be used.

The interaction of exogenous agents, such as water or other agents, with natural vernix is related to the nonpolar (dispersive) and polar (nondispersive) components of vernix and the critical surface tension (CST) of vernix. Water has a relatively high CST (72 dynes/cm). The hydrophobicity (i.e., relatively low CST) of vernix was unanticipated, because about 80% by weight of natural vernix is water. The nonpolar component (lipids) of vernix is substantially higher than the polar component (cells, which contribute proteins), and confers hydrophobicity to vernix because the lipid component is a continuous phase surrounding the cellular components with which water is associated. In comparison to a known hydrophobic material and skin protectant, petrolatum, which has an extremely high nonpolar component, the nonpolar component of natural vernix is only slightly lower. In addition, the CST of both vernix and petrolatum are comparable. As a result, application of vernix to a surface such as skin, either normal skin or compromised skin (for example, wounded, abraded, cut, punctured, etc.), protects the surface from the effects of water exposure.

A result of the low CST of vernix is that little interaction between vernix and hydrophilic liquids would be expected to occur. For example, there would be expected to be little interaction between a vernix-treated surface, such as skin or a substrate to which natural vernix has been provided, that is exposed to an exogenous hydrophilic liquid, such as water, saline, urine, etc. The low CST of vernix imparts a hydrophobic character to vernix with respect to these liquids, and hence vernix serves as a protectant against the effects of these liquids.

The water in native vernix is associated with cells, and the cells are embedded within the lipid material, thus, the lipid component presents vernix to the environment. However, if the lipid fraction is removed either partially or totally by exposure to hydrophobic agents, then the water rich fraction, such as cells, could be exposed to the environment. The inventive simulated vernix composition may be regulated to have a higher polar component to repel nonpolar agents. This composition protects nonpolar materials, even after the hydrophobic lipid components are modified through interaction with the environment.

Native vernix protects the developing skin from the deleterious effects of substances, such as water, urine, and feces, present in utero during gestation. The inventive composition may be applied to any biological surface whereby a surface energy of about 40 dynes/cm is beneficial for repeling exogenous agents. Thus, an effective amount of simulated vernix is that which achieves a surface free energy of about 40 dynes/cm, to a minimum of about 20 dynes/cm. For example, applying the inventive composition in an effective amount to the diaper area protects the skin from the damaging effects of fecal material. Feces contain protease and lipase enzymes which can damage the skin surface upon contact. Lowering the surface energy of this skin surface by applying the inventive composition protects the skin against contact with the water-containing feces.

Examples of simulated cells that may be used in the inventive composition include, but are not limited, to cubosomes, phospholipid liposomes, nanoparticles, microparticles, colloidosomes, non-phospholipid liposomes (Catezomes®), cultured cells, etc. Each of these may be loaded with hydrophilic molecules to enhance hydration. Hydrophilic molecules include but are not limited to glycerin, lactic acid, pyrrolidone carboxylic acid, urocanic acid, and proteins which, as previously defined; include amino acids such as NMF. Each of these may also contain hyaluronic acid as an additional water binder and to control the viscosity of the composition.

Bicontinuous cubic phase liquid crystals (cubosomes) may be used. Cubosomes are dispersed nanostructured particles of cubic phase liquid crystals with controlled release properties. The surfactant assembles into bilayers that are twisted into a periodic, three-dimension periodic minimal surface, forming a tightly packed structure that is "honeycombed" with bicontinuous domains of water and lipid. This structure accommodates water-soluble, lipid-soluble, and amphiphilic molecules.

Three bicontinuous liquid crystal structures are common: $P_{n3m}$ (D-surface), $I_{a3d}$ (G-surface), and $I_{m3m}$ (P-surface). These can be described in terms of nodal surfaces. Bicontinuous cubic phases are found in natural lipids, cationic and nonionic surfactants, and polymer systems, although the lipid most widely used to construct bicontinuous cubic phases is the monoglyceride monoolein. Following the phase diagram of Qiu and Caffrey, *Biomaterials* 21;223(1999), which is expressly incorporated by reference herein in its entirety, monoglycerides spontaneously form bicontinuous cubic phases upon the addition of water, are relatively insoluble (allowing the formation of colloidal dispersions of cubosomes), and are resistant to temperature changes.

Actives can be loaded by direct addition to melted lipid or water (i.e., before hydration), or by diffusion into the structure after it is formed. The structure generally maintains the efficacy of the actives and may help stabilize actives such as vitamins and proteins. The upper limit to loading lipid-soluble actives is typically about 10 wt.% (relative to the cubic phase), which is governed by the loss of cubic phase structure upon addition. The actives may be controllably delivered where diffusion is governed by the tortuous diffusion of the active through the "regular" channel structure of the cubic phase.

Cubosomes are thermodynamically stable and can last indefinitely provided there is no hydrolysis of the liquid. Colloidal dispersions of cubosomes may be stabilized by adding polymers. Cubosomes are fabricated from monoglycerol long chain saturated fatty acids, typically monoolein, and water. The ratio of monoolein/water may variable, for example, 60/40, 65/35, 70/30, 75/25, etc., such that it produces a cubosome phase. For example, if the composition contains 20% lipid and 5% protein, the cubosome/water component would constitute 75% of the total composition. Thus, the concentration of lipid in the total composition does not include the concentration of monoglycerol in the cubosome. A cubosome of 60% monoolein ($C_{17}$) 40% water gel may be preaired. Cubosomes are made by nucleation according to methods provided in *Langmuir* 17;5748(2001) which is expressly incorporated by reference herein in its entirety.

A first method of fabricating and stabilizing cubosomes involves high shear dispersion of bulk cubic liquid crystalline material into submicron particles. A second method involves simple mixing of two water-like solutions with minimal input of energy. This method results in cubosomes that are smaller and more stable than those produced by the first method. Monoolein, used to form cubic liquid crystals and essentially insoluble in water, is mixed with a hydrotrope which dissolves the lipid to create a water-like solution with a decrease of solubility. Cubosomes form spontaneously as long as the dilution trajectory (using a phase diagram of monoolein-ethanol-water) falls into a cubic phase-water miscibility gap. Besides monoolein, any lipid and hydrotrope combination which form cubic liquid crystalline material upon dilution may be used. Actives and stabilizers can be formulated into the lipid and/or hydrotrope to produce colloidally stabilized, controlled-release dispersions. A third method of spray drying produces dry powder cubosome precursors. Starch-encapsulated monoolein is produced by spray drying a dispersion of cubic liquid crystalline particles in an aqueous starch solution. Dextran-encapsulated monoolein is produced by spray drying an emulsion formed by an ethanol-dextran-monoolein-water system. The starch and dextran decrease powder cohesion during drying and act as a soluble colloidal stabilizer upon hydration of the powders. Both powders form colloidally-stable cubosomes with an average size of 0.6 μm upon addition to water. This method allows the surface state of the cubosomes to be tailored to particular uses. For example, cubosomes can be loaded with surfactant protein to provide anti-oxidant and anti-infective properties.

As previously stated, other types of vesicles or vehicles may be used as simulated cells. Phospholipid liposomes may encapsulate water and, optionally, also encapsulate water-soluble components. They may be coated with polyethylene glycol (PEG) to further enhance their hydrophilic properties.

Nanoparticles may also be used, for example, a polyvinyl alcohol hydrogel with a diameter in the range of about 500 nm to about 750 mn; a poly-N-isopropylacrylamide hyorogel (50 nm to 1 µm); a copolymer of poly(ethylene oxide)-poly(L-lactic acid); or poly(L-lactic acid) coated with poly(ethylene oxide).

Microparticles may also be used, such as poly(lactide-co-glycolide) and PEG-dextran conjugates in the range of about 400 nm to about 600 nm. A lipid multilayer which encapsulates water may also be used.

Colloidosomes may also be used. Colloidosomes are spherical shells of micron-sized colloidal particles that are formed when colloidal particles are introduced to emulsion droplet templates. They self-assemble on the surface of the droplets in order to minimize the total interfacial energy by eliminating part of the interface. When many particles self-assemble, the result is a six-fold two-dimensional crystalline structure. Colloidosomes are also selectively permeable, allowing sub-micron particles to diffuse in, but excluding larger micron-sized particles. They can also be made selectively permeable to particles of different sizes.

Non-phospholipid liposomes (Catezomes®), Collaborative Laboratories, Inc. East Setauket N.Y.), which are composed of fatty acid salts of quartemary amines may also be used. Their structure permits the incorporation of both hydrophilic and hydrophobic materials because the salt bond region of the molecule is hydrophilic and the alkyl chain region of the molecule is hydrophobic. Release of encapsulated material is controlled by regulating the ionic strength of the surrounding medium at the time of delivery to the skin.

Cultured cells may also be used. The cells may be disaggregated (using either chemical or mechanical disaggregation methods), engineered, loaded with hydrophilic molecules, etc. Any of these structure may also contain hyaluronic acid, which controls viscosity and also adds an additional water-binder.

In one embodiment, the inventive composition is applied to a physiologically acceptable support structure in a liquid state to form a film. It is presented as droplets which coalesce to form a film upon encountering the support. A film is defined herein as an interfacial surface covering, in either a liquid or a solid state, with temperature-dependant properties. Film-forming techniques include but are not limited to spraying, extruding, blowing, pouring, evaporating, coating and painting.

In an alternate embodiment, a preformed film of the inventive composition is applied to a physiologically acceptable support. The physiologically acceptable support is one that can withstand sterilization, preferably by standard sterilization techniques known to one skilled in the art such as exposing to gamma radiation, autoclaving, and so on. The support is not limited to a particular composition or configuration and, depending upon its use, may or may not be sterilized and may take various forms. In one embodiment, the film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II® (Sterling Drug Inc., New York N.Y.) or circular nylon filters of suitable porosity (Micron Separations Inc., Westboro Mass.). Other support materials, however, may also be used to practice the invention.

In another embodiment, the film of the inventive composition is used to promote wound healing and/or tissue repair. It may be applied to various materials for placement either in direct contact or indirect contact with an intact or compromised skin site requiring treatment, such as a wound, an abrasion, an ulcer, a burned area, a site of infection or irritation, a wart etc. The support may be permeable to physical and/or chemical agents, and may take a variety of forms, depending upon its purpose and the extent of the area requiring dressing or treatment. The film may be applied to various synthetics such as thermoplastic films, blown films and breathable films, and various natural and synthetic fabric compositions such as woven, non-woven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

The inventive composition may be used therapeutically to promote skin growth, skin maturation, skin barrier formation, wound healing, skin flexibility, and tissue repair. It may also be used as a skin protectant to promote skin barrier formation, skin moisture retention, and skin flexibility.

The inventive composition has an overall neutral pH. The simulated cell component and/or added amino acids have a general acidic pH. The inventive composition has a viscosity profile, a rheology profile, penetrability, and water vapor transport properties that is substantially similar to native vernix.

As reported in U.S. patent application Ser. No. 09/850,844, which is expressly incorporated by reference herein in its entirety, contact angle (degrees) data for fresh and 7-week old vernix and a petrolatum control are as follows:

|  | Fresh vernix | | 7-week old vernix | | Petrolatum | |
| --- | --- | --- | --- | --- | --- | --- |
|  | Angle | SD | Angle | SD | Angle | SD |
| Benzyl Alcohol | 21.8 | 2.9 | 19.6 | 1.6 | 34.4 | 3.0 |
| Diiodomethane | 36.2 | 2.1 | 31.8 | 1.8 | 38.4 | 2.2 |
| Glycerol | 74.3 | 1.9 | 74.2 | 2.3 | 79.1 | 2.1 |
| Water | 83.5 | 0.8 | — | — | — | — |

The inventive composition having a protein component in the range of about 5% of the total composition to about 30% of the total composition, a lipid component in the range of about 5% of the total composition to about 30% of the total composition, and a water/simulated cell component constituting the remainder of the total composition, provides a composition having contact angles with the above agents which simulates those of native vernix. Specifically, the composition provides a contact angle with benzyl alcohol in the range of about 18.0 to about 24.7; a contact angle with diiodomethane in the range of about 30.0 to about 38.3; a contact angle with glycerol in the range of about 71.9 to about 76.5; and a contact angle with water in the range of about 82.7 to about 84.3.

Also as reported in U.S. patent application Ser. No. 09/850,844, the Critical Surface Tension (CST) of fresh vernix and seven week old vernix was determined, along with that of a petrolatum control. The results are indicated in the following table:

|  | CST (dyne/cm) |
| --- | --- |
| Fresh vernix (dynamic θ) | 40.47 |
| Fresh vernix (static θ) | 38.65 |
| 7-week old vernix (static θ) | 39.80 |
| Petrolatum (static θ) | 35.79 |

The synthetic vernix on a skin surface provides a CST of about 38 dynes/cm to about 41 dynes/cm and a CST greater than at least 36 dynes/cm.

CST is a "wettability index" that indicates the minimum value of surface tension needed for a liquid to spread completely (that is, have a contact angle of zero), on a particular surface material. Any liquid whose surface tension is equal to or less than the CST will make a zero contact angle (θ=0, Cos θ=1), and will completely spread on the surface, while any liquid having a surface tension greater than the CST will form drops with a finite contact angle.

The inventive composition having a protein component in the range of about 5% of the total composition to about 30% of the total composition, a lipid component in the range of about 5% of the total composition to about 30% of the total composition, and a water/simulated cell component constituting the remainder of the total composition, provides a composition having a CST which simulates those of native vernix.

Also as reported in U.S. patent application Ser. No. 09/850,844, the Surface Free Energy (SFE) of the polar component of fresh native vernix was 1.48 dynes/cm, while petrolatum had almost no polar SFE (0.03 dynes/cm). These results indicate that the main component of the vernix surface free energy was dispersive, that is, nonpolar. The nonpolar component in vernix was slightly lower than that of petrolatum, which has an extremely low polar component.

The inventive composition having a protein component in the range of about 5% of the total composition to about 30% of the total composition, a lipid component in the range of about 5% of the total composition to about 30% of the total composition, and a water/simulated cell component constituting the remainder of the total composition, provides a composition having a SFE which simulates those of native vernix.

Also as reported in U.S. patent application Ser. No. 09/850,844, native vernix provides barrier properties in the range of those of semipermeable films such as Vigilon®, Exxaire®, Silon®, and Flexzan®, and provided an intermediate level of hydration. An intermediate level of hydration provided the optimum environment for barrier repair to occur, compared to either a high or low level of hydration.

The inventive composition thus has barrier properties which simulate those of native vernix.

The invention will be further appreciated with reference to the following examples.

EXAMPLE 1

Cubosomes of monoolein and water (60% monoolein, 40% water) are produced. The resulting cuboidal gel is further processed to produce a dispersion of smaller cubosome particles. The particles are mixed into the lipid phase of cholesterol esters (about 20% to about 35%), ceramide (about 10% to about 20%), triglycerides (about 10% to about 20%), cholesterol (about 5% to about 10%), FFA (about 5% to about 10%), phospholipids (about 5% to about 10%), wax esters (about 2% to about 8%), squalene (about 0.5% to about 5%), wax diesters (about 0.5% to about 6%), and cholesterol sulfate (about 0.1% to about 3%). The water phase of the cubosome may be loaded with hydrophilic molecules (glycerin, lactic acid, pyrrolidone carboxylic acid, urocanic acid, amino acids) to provide a source of water binding materials.

EXAMPLE 2

The synthetic vernix composition is prepared as in Example 1 using cubosomes of monoglycerol of long chain saturated fatty acids (e.g., $C_{22}$ chain length).

EXAMPLE 3

The synthetic vernix composition is prepared as in Example 1 replacing cubosomes with phospholipid liposomes, nonphospholipid liposomes, colloidosomes, nanoparticles, or microparticles.

Liposomes may be single or multiple lipid layers to encapsulate water, and coated on the outside with polyethylene glycol to provide additional water to the system. The water phase can also include water soluble components. Nanoparticles may be polyvinyl alcohol hydrogel, about 500 nm to about 750 nm in diameter. Nanoparticles may also be poly-N-isopropylacrylamide (pNIPAm) hydrogel; these are monodisperse hydrogel particles with sizes from 50 nm to 1 μm in diameter. Nanoparticles may further be poly(ethylene oxide)-poly(L-lactic acid) as a copolymer system. Nanoparticles of poly(L-lactic acid) may be coated with polyethylene oxide. Microspheres may be about 400 nm to about 600 nm in diameter containing poly(lactide-co-glycolide) to which polyethylene glycol dextran conjugates are added. Microspheres may encapsulate water to which a lipid multilayer has been added.

EXAMPLE 4

The synthetic vernix compositions may be prepared according to any of Examples 1-3, with hyaluronic acid added to provide additional water binding materials and to control viscosity of the composition.

EXAMPLE 5

Cubosomes with controlled release properties are prepared as described in *J. Colloid Interface Science* (2003) in press, except that natural moisturizing factor (NMF) is substituted for ketoprofen.

About 0.5 g monoolein is melted into the bottom of a 1000 ml glass cylinder. Surfactant and NMF are dissolved into the melt. Sufficient buffer is added to the monoolein to form the cubic phase liquid crystal. Once formed, an additional 50 ml buffer is added to the cylinder. An overhead propeller briskly stirs the solution above the liquid crystal. This arrangement has a one-dimensional diffusion profile with the diffusion of NMF through the gel as the rate-limiting step. Small aliquots of buffer are periodically removed, and the concentration of NMF is determined by spectrophotometric analysis at light of UV/visible wavelength.

EXAMPLE 6

Loaded solid lipid nanoparticles for topical application are prepared according to the method in *Eur. J. Pharmaceutics*

*Biopharm* 49 (2000) 211, which is expressly incorporated herein by reference, except that NMF is substituted for vitamin A.

Solid lipid nanoparticles and nanoemulsions are prepared with 5% NMF (with respect to the lipid). Glyceryl monooleate was melted at 85° C. and NMF was added. The hot lipid phase was dispersed in a surfactant solution and a premix was formed using an ultra turrax (IKA, Staufen Germany). The premix was passed through a Lab 60 high pressure homogenizer (APV Gaulin Lübeck Germany). Two cycles at 500 bar and 85° C. were performed. Nanoemulsions were prepared in the same manner except that Miglyol 812 was substituted for glyceryl monooleate. In either nanoparticles or nanoemulsions, the final concentration of NMF was 0.5%.

EXAMPLE 7

Polymersomes, as described by Discher et al., Science (2003) in press, which is expressly incorporated by reference herein in its entirety, are made from amphilic diblock copolymers. These polymers may be polyethyleneoxide-polyethylethylene ($EO_{40}$-$EE_{37}$). The membrane is at least tenfold less permeable to water than the phospholipid bilayers of liposomes and is used to provide the water handling profile of natural vernix, specifically, regulation of water vapor transport and rate of water loss.

EXAMPLE 8

Poly (DL-lactide-co-glycolide) (PLGA) nanoparticles without surfactant are prepared by a dialysis method as described in *J. App. Polymer Sci.* 80 (2001) 2228, which is expressly incorporated by reference herein in its entirety. The PLGA nanoparticles are loaded with proteins, peptides, and/ or amino acids, such as epidermal growth factor, NMF, etc., and water.

EXAMPLE 9

Poly(glutamic acid) poly(ethyleneglycol) hydrogels are prepared as described in *J. Biomed. Mater. Res.* 62 (2002) 14, which is expressly incorporated by reference herein in its entirety. Poly(glutamic acid) is the polymer backbone and poly(ethylene glycol) is the crosslinker. The hydrogels are synthesized using photo-initiated crosslinking chemistry and are loaded with proteins, peptides, and/or amino acids, such as epidermal growth factor, NMF, etc. and water.

EXAMPLE 10

Protein for controlled release is encapsulated in poly(lactide-co-glycolide) (PLGA) as described in *Nature Biotechnology* 18 (2002) 52, which is expressly incorporated by reference herein in its entirety. For PLGA microcylinder preparation, the protein, as previously defined, is suspended, with or without basic salt, in acetone-PGLA. The suspension is loaded into a syringe and extruded into silicone rubber tubing. The solvent extruded suspension is dried at room temperature and then under vacuum. For PLGA microsphere preparation, the protein in 10 mM phosphate buffer (pH 7.4), with or without basic salt, is added to a solution of PLGA/ $CH_2Cl_2$ and homogenized at 10,000 r.p.m. and transferred to a 2% polyvinyl alcohol (PVA) solution. A water-in-oil-in-water emulsion is formed by vortexing. The particles are hardened in 0.5% PVA and are collected by centrifugation, washed, and lyophilized.

EXAMPLE 11

A highly porous polyglycolide is prepared using a solid state condensation reaction as described in *Macromol. Chem. Phys.* 200 (1999) 2221, which is expressly incorporated by reference herein in its entirety. Ground sodium chloroacetate is heated with constant stirring at either 160° C. or 180° C. Polyglycolide is washed with water to remove residual sodium chloroacetate and formed sodium chloride.

Exogenously applied physiologically compatible vernix removes soil from the skin with an effectiveness that is quantitatively at least equivalent to, and may be better than, commercial skin cleansers. Vernix on the skin surface interacts with exogenous cleansing agents such as soaps and/or surfactant, with subsequent flocculation and detachment, consistent with a function of vernix as an endogenous skin cleanser at birth. A soap, as used herein, is a mixture of sodium salts of long chain fatty acids, typically $C_{12}$ to $C_{18}$ fatty acids. A surfactant, as used herein, is a surface-active substance. Both soaps and surfactants are cleansing agents.

The cleansing aspects of isolated vernix were evaluated. In one study, 10 mg of soiling material in the form of uniform black carbon particles (toner from a photocopier) were applied to normal adult volar skin (area=16 $cm^2$). This was followed by manual application and removal of about 2 mg/$cm^2$ of irradiated vernix or selected skin cleansers (Pond's Cold Cream™ and Johnson & Johnson Baby Wash™). Removal of soil was quantified as a change in light intensity, using L-scale analysis of digital images. In another study, vernix was applied to human cadaver skin, with no vernix or vernix film thicknesses ranging from 2 mg/$cm^2$ to about 16 mg/$cm^2$. The skin sections were mounted in Franz diffusion cells and exposed to 0.25% $^{w/v}$ sodium lauryl sulfate (SLS), a common surfactant found in soap solutions. Following 24 hours of exposure, flocculation of vernix was measured spectrophotometrically as solution turbidity at 600 nm.

Vernix was collected from the skin surface of term newborn infants and stored at 4° C. until use. Samples contaminated with blood and/or meconium were discarded. Digital images of adult hand and volar forearm were recorded at 30× magnification using a Skin Surface Analyzer (Moritex USA, Inc.) which captures digital images between 10× through 700× magnification and can be operated using two different modes of illumination. One mode supplies light en faces, rendering precise surface detail. The second mode illuminates the skin via back-scattered light, resulting in polarization of the light source; this is useful when specular reflectance from the skin surface interferes with image analysis.

For the cleansing assay, 10 mg of the previously described soiling material was uniformly applied to pre-cleaned normal adult hand and volar forearm skin (area=16 $cm^2$). This was followed by manual application and removal of 12.5 mg/$cm^2$ of a topical cleansing preparation, either irradiated vernix, Pond's Cold Cream™, or Johnson & Johnson Baby Wash™. All applications and removals used manual pressure under routine conditions. High resolution digital photographs were obtained with a Kodak DCS 420C digital camera before and after applying the soiling material, and after cleansing.

Digital images obtained during cleansing were analyzed to assess efficacy of vernix and the two commercially available topical cleansing preparations. Soil removal was quantified by processing the images in two ways. In one way, the change in light intensity was quantitated using Adobe Photoshop L-scale analysis. In the other way, a program was written using Matlab technical computing software (The Math Works, Natick Mass.), whereby the original digital image was first segmented into 16 equally sized regions and then converted to Gray scale. A threshold algorithm was performed on each region to distinguish between soiling material and background features of the skin. This process generated a black and white image that was used to calculate the percent of the region that was covered with the soiling material. Statistical comparisons between treatment groups were performed using one-way ANOVA.

Table 1 provides representative data from both the L-scale analysis and Gray scale analysis from one representative experiment There surface evaluated was either clean (pre-treatment), fully soiled, fully soiled and treated with the indicated cleansing agent, evaluated after cleansing with the indicated agents (Aquaphor, Johnson & Johnson Baby Wash™, Pond's Cold Cream™, vernix, water), or evaluated after cleansing with alcohol.

TABLE 1

| IMAGE | L-SCALE Mean | SD | GRAY SCALE Mean | SD | CLEANSING AGENT |
|---|---|---|---|---|---|
| pre-treatment | 192 | 5 | 185 | 6 | Aquaphor |
| fully soiled | 83 | 17 | 77 | 16 | |
| fully soiled plus treatment | 65 | 16 | 61 | 14 | |
| post-treatment cleaning | 174 | 7 | 166 | 8 | |
| post alcohol cleaning | 154 | 7 | 145 | 7 | |
| pre-treatment | 197 | 5 | 191 | 6 | Johnson & Johnson Baby Wash ™ |
| fully soiled | 129 | 17 | 121 | 17 | |
| fully soiled plus treatment | 54 | 12 | 51 | 10 | |
| post-treatment cleaning | 182 | 6 | 175 | 7 | |
| post alcohol cleaning | 196 | 4 | 190 | 4 | |
| pre-treatment | 182 | 7 | 175 | 8 | Ponds Cold Cream ™ |
| fully soiled | 108 | 14 | 99 | 14 | |
| fully soiled plus treatment | 77 | 19 | 71 | 17 | |
| post-treatment cleaning | 197 | 5 | 191 | 6 | |
| pre-treatment | 120 | 5 | 112 | 4 | Vernix |
| fully soiled | 85 | 18 | 79 | 16 | |
| fully soiled plus treatment | 41 | 7 | 40 | 6 | |
| post-treatment cleaning | 135 | 5 | 126 | 5 | |
| post alcohol treatment | 120 | 5 | 112 | 4 | |
| pre-treatment | 193 | 5 | 187 | 6 | Water |
| fully soiled | 53 | 16 | 50 | 14 | |
| fully soiled plus treatment | 96 | 25 | 89 | 23 | |
| post-treatment cleaning | 183 | 7 | 175 | 7 | |
| post alcohol treatment | 162 | 7 | 154 | 7 | |

Figure 1B:
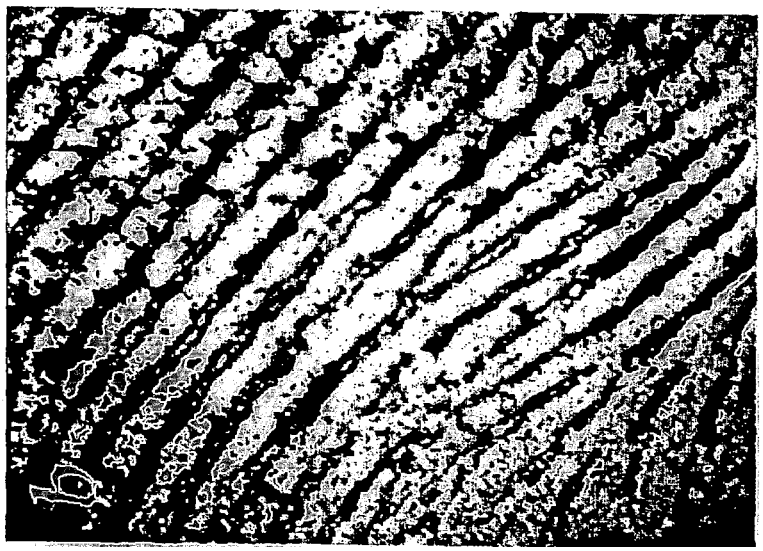
Figure 1A:
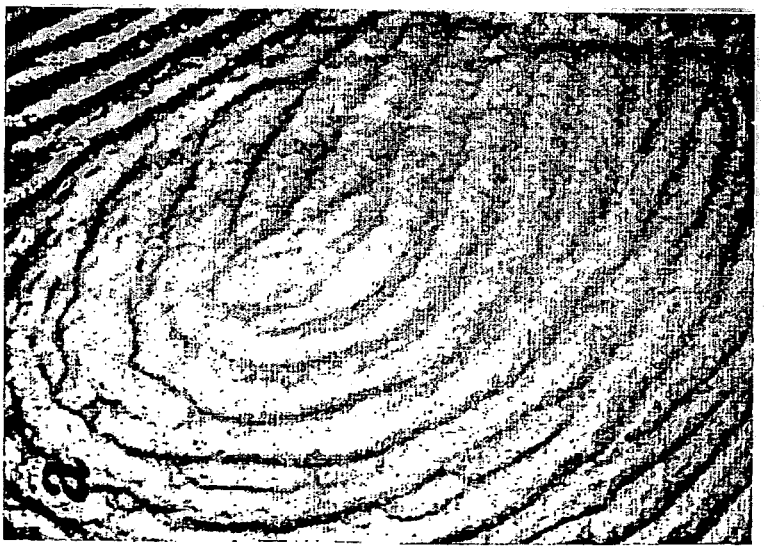
Figure 2A:
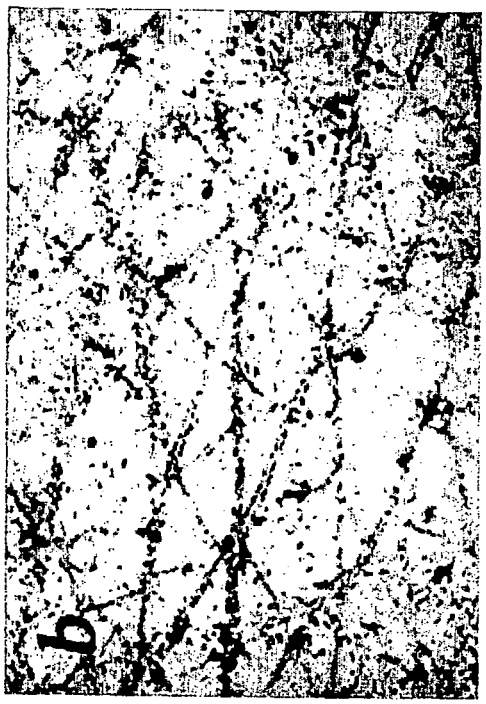
FIGS. 2A, 2B, 2C, and 2D are digital images of volar forearm skin, either unsoiled (FIG. 2A), after application of a soiling material (FIG. 2B), or after application of either vernix (FIG. 2C) or a commercial soap (FIG. 2D) to the soiled area.
Figure 2B:
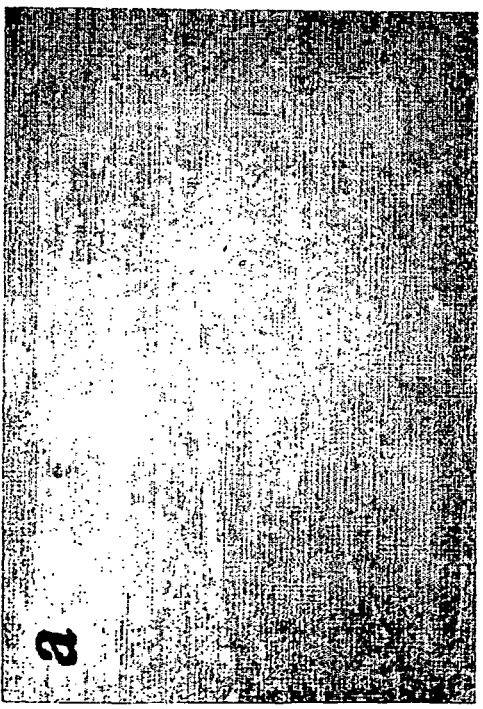
Figure 2C:
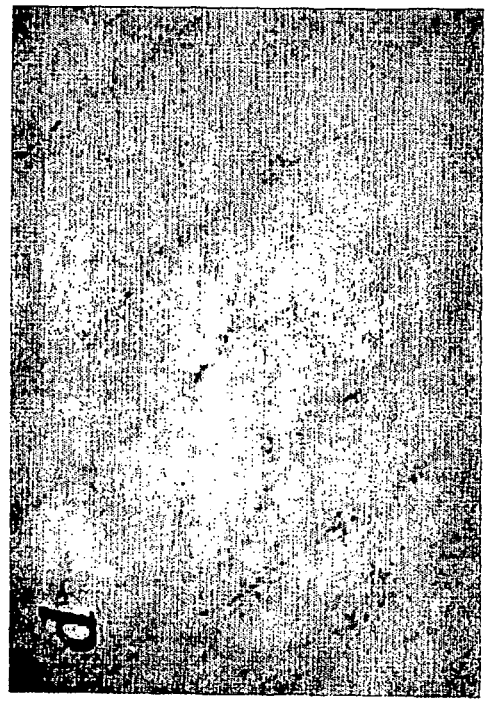
Figure 2D:
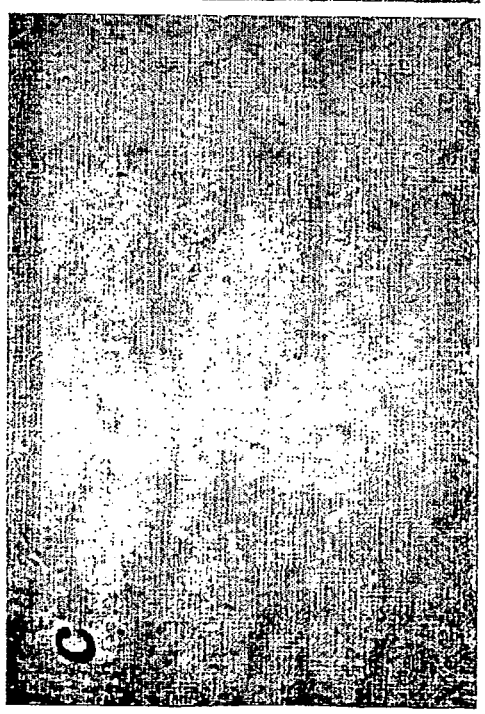
Figure 3A:
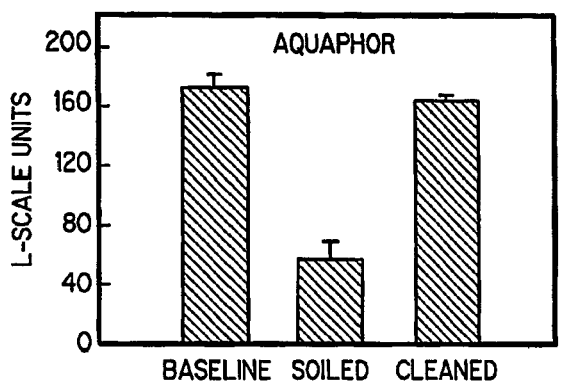
FIGS. 3A, 3B, 3C, and 3D are histograms quantitating the amount of soiling material on the skin surface of unsoiled (baseline), soiled, and cleansed skin treated with Aquaphor (FIG. 3A), commercial cleansers (FIGS. 3B and 3C), or vernix (FIG. 3D).
Figure 3B:
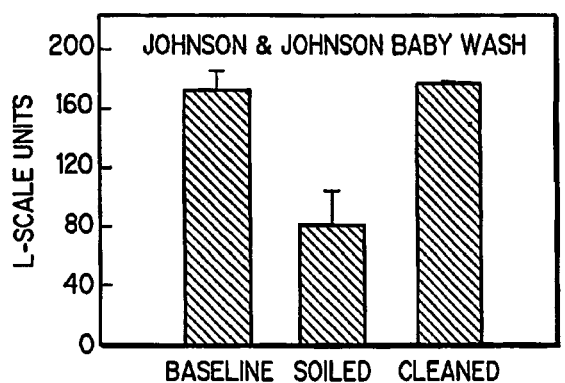
Figure 3C:
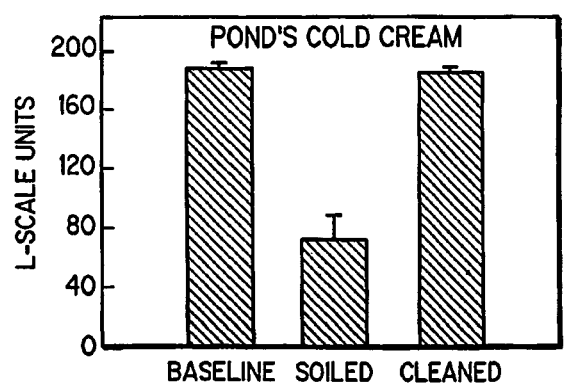
Figure 3D:
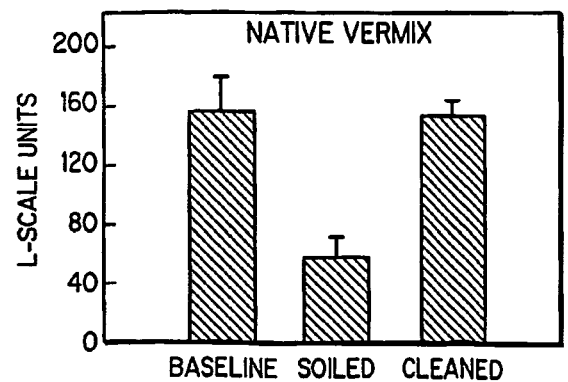
Figure 4A:
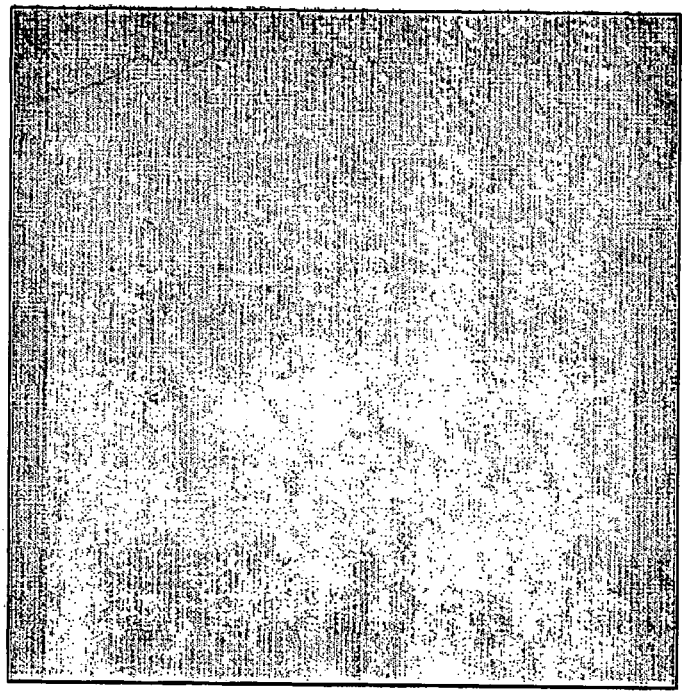
FIGS. 4A, 4B, 4C, and 4D are digital images of skin before soiling and after cleaning with Aquaphor (FIG. 4A), commercial cleansers (FIGS. 4B and 4C), or vernix (FIG. 4D).
Figure 4A:
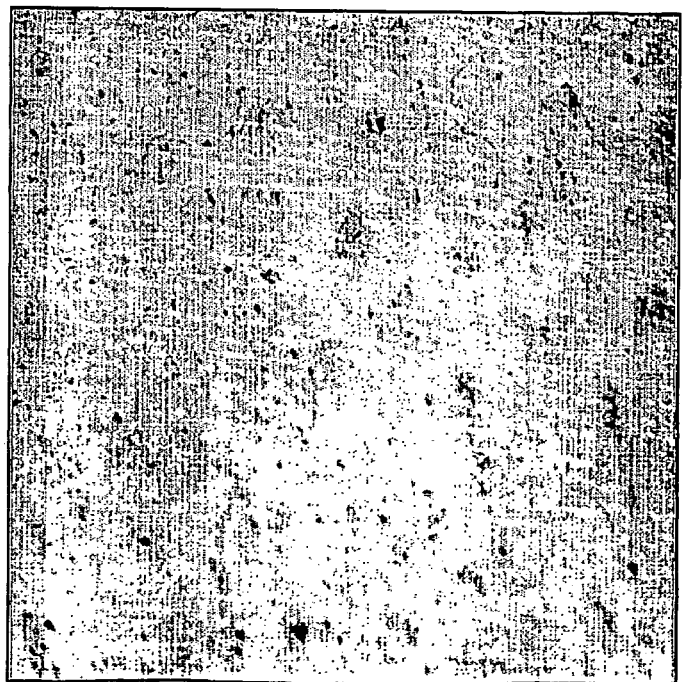
Figure 4B:
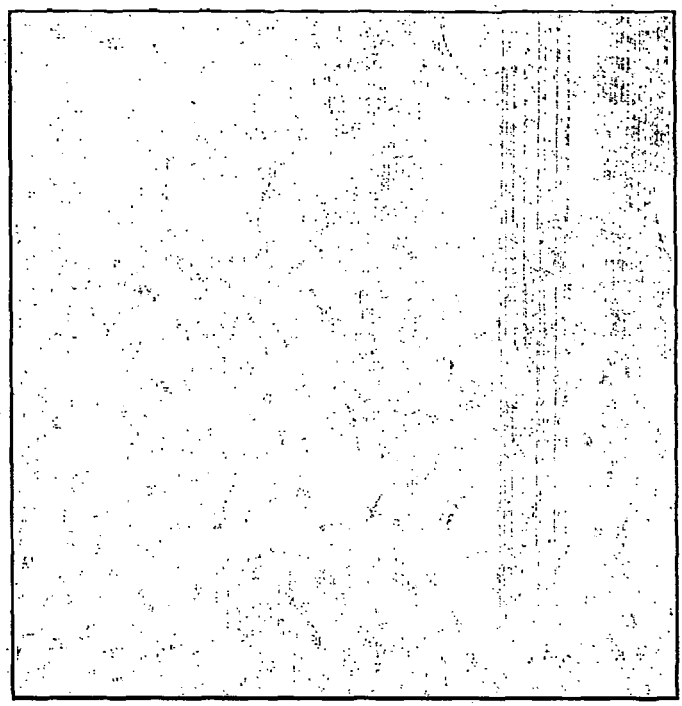
Figure 4B:
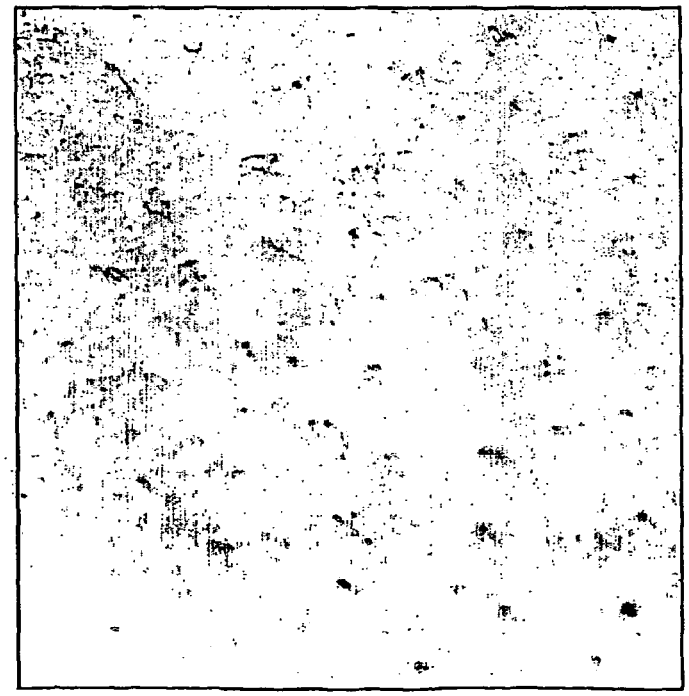
Figure 4C:
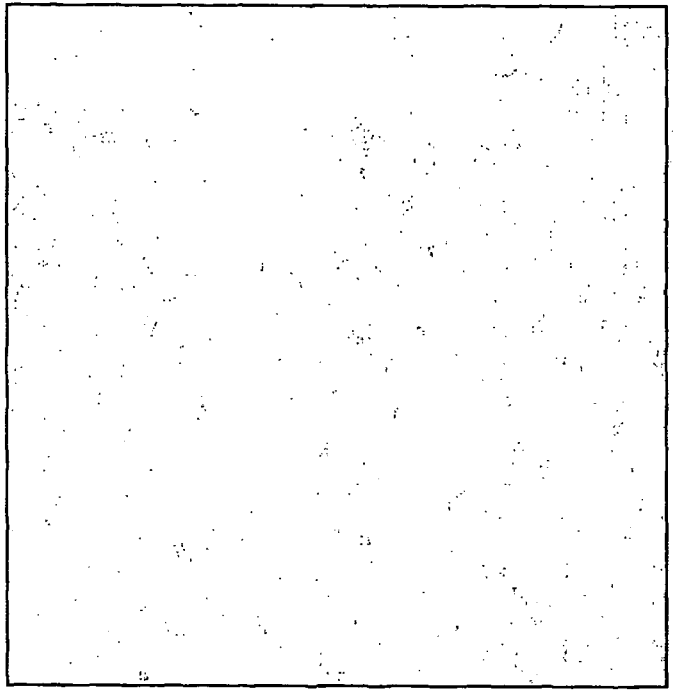
Figure 4C:
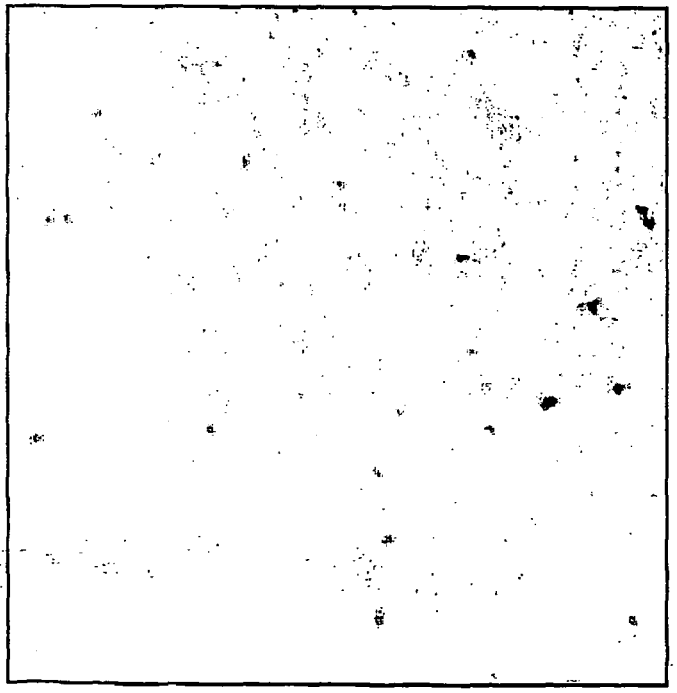
Figure 4D:
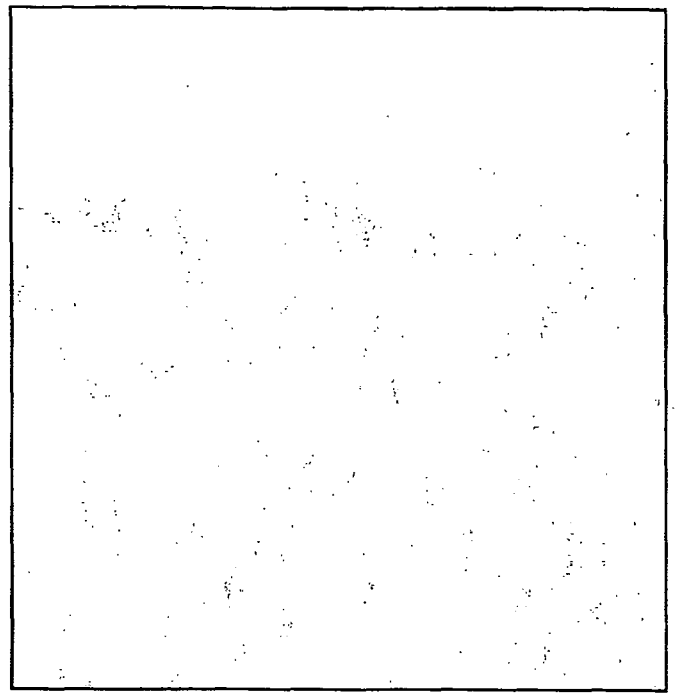
Figure 4D:
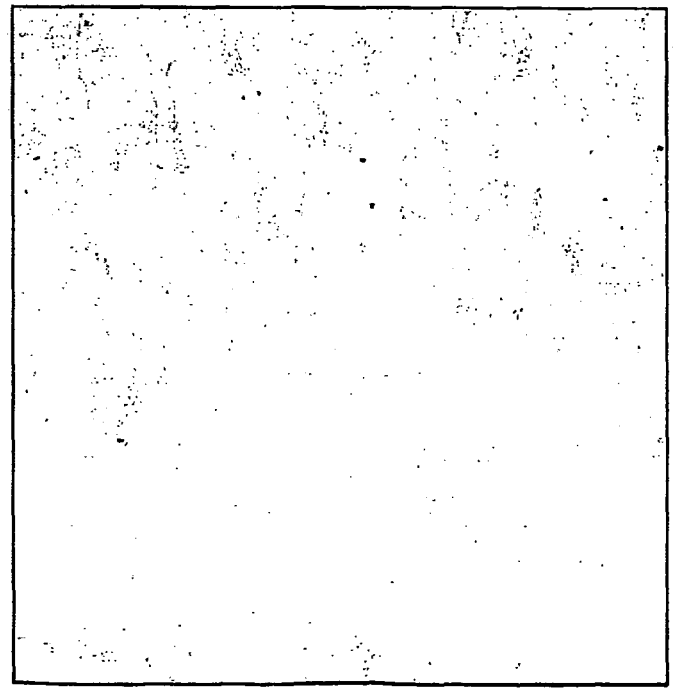

FIG. 1A demonstrates the cleansing capacity of vernix. Digital images of the hand were recorded at 30× magnification using a Skin Surface Analyzer, as previously described. This set of images was obtained using en faces illumination of the skin. FIG. 1A shows the unsoiled skin surface. FIG. 1B shows the skin after application of the carbon particulate soiling material. The carbon particles remain lodged in the furrows and pores of the skin and in the sweat glands. FIG. 1C shows the soiled skin after application of vernix, whereby no carbon particles are visible in any skin area, including furrows and pores.

FIG. 2 also demonstrates the cleansing capacity of vernix. The figures were obtained using the same conditions described previously, with the exception that volar forearm skin was used and a light source that provides illumination through the skin, rather than from above, was used. FIGS. 2A, 2B, and 2C show the unsoiled, carbon-soiled, and vernix-cleansed skin, respectively. FIG. 2D shows an area of the soiled skin after washing the surface with a commercially available liquid hand soap instead of vernix.

To quantitate the amount of soiling material on the skin surface, L-score values of volar forearm skin were obtained. Adult volar forearm was assessed using Adobe Photoshop L-scale analysis of digital images. With reference to FIG. 3, data were collected before soiling (baseline), after soiling material was manually rubbed into the skin (soiled), and after cleansing (cleaned). The cleansing treatments were either Aquaphor, Johnson & Johnson Baby Wash™, Pond's Cold Cream™, or vernix. The results are shown in FIGS. 3A, 3B, 3C, and 3D. The data demonstrate that all of the tested cleansing agents returned the skin to near baseline L-scale levels.

As shown in the following table, when using L-score data to compare baseline (pre-soiled) and cleaned volar forearm skin, one-way ANOVA revealed no statistically significant differences between the tested cleansing agents.

TABLE 2

Comparison of Pre-Soiled and Cleaned Skin Using One-way ANOVA

| | Cleaning Material | | |
|---|---|---|---|
| | Pond's Cold Cream ™ | Johnson & Johnson Baby Wash ™ | Native Vernix |
| Mean | 0.47% | 1.19% | 0.22% |
| Standard Error of the Mean (SEM) | ±0.08 | ±0.15 | ±0.03 |
| Number of Samples (N) | 48 | 48 | 48 |

These data indicate that all of the topical cleansers adequately clean the skin surface. While Johnson & Johnson Baby Wash™ and Pond's Cold Cream™ are routinely used to cleanse the skin, the use of the natural vernix biofilm has not previously been reported.

FIG. 4 shows digital images of skin before soiling and after treatment with one of four cleansing agents: Aquaphor (FIG. 4A), Johnson & Johnson Baby Wash™ (FIG. 4B), Pond's Cold Cream™ (FIG. 4C), or vernix (FIG. 4D). The images were obtained as previously described for FIG. 2. For each treatment, soiling material is visible on the skin after cleansing. Soiling material in pores is seen as punctate material, and soiling material on hair is seen as diffuse streaks. By visual inspection of the images, the vernix treated skin appeared to have the most soiling material removed.

Figure 5:
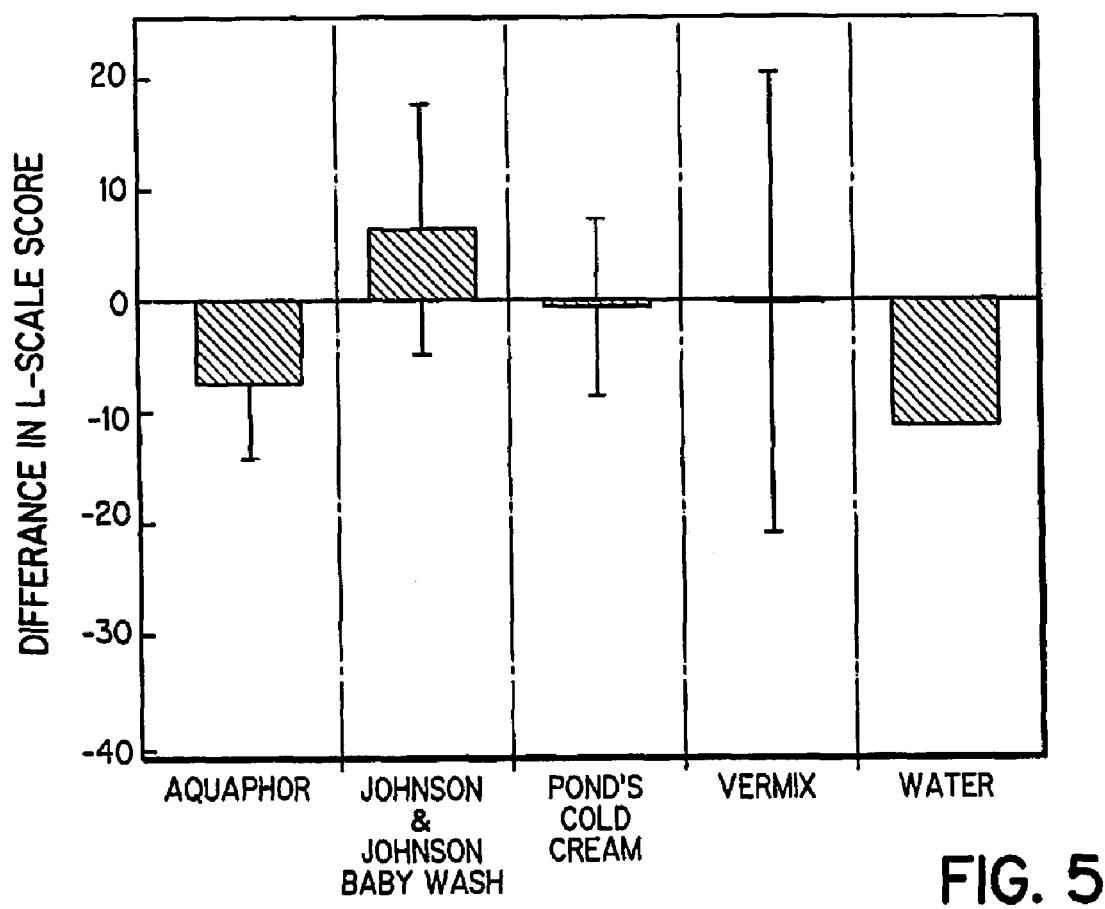
FIG. 5 is a plot of differences in L-scale scores before and after cleansing with various treatments.

FIG. 5 quantitates the results from FIG. 4 as differences in L-scale scores before and after cleansing. A negative value indicated that skin retained some soiling material, with higher negative values indicating more soiling material retained. A positive value indicated that the skin was cleaner after the cleansing procedure. Approximate values for each treatment were as follows: Aquaphor −8; Johnson & Johnson Baby Wash™ +7; Pond's Cold Cream™ −1; vernix<−0.5; and water −11. These comparative data indicate that water and Aquaphor treatments leave the skin slightly "dirtier"; Johnson & Johnson Baby Wash™ leaves the skin "cleaner"; and Pond's Cold Cream™ and vernix remove the soiling material equally well.

The percent coverage determination is another measure of cleansing efficacy. One-way ANOVA of these data showed that vernix cleansing resulted in a significantly less amount of soiling material residue, compared to Johnson & Johnson Baby Wash™ ($p<0.05$) No other significant differences between groups were observed.

Figure 6:
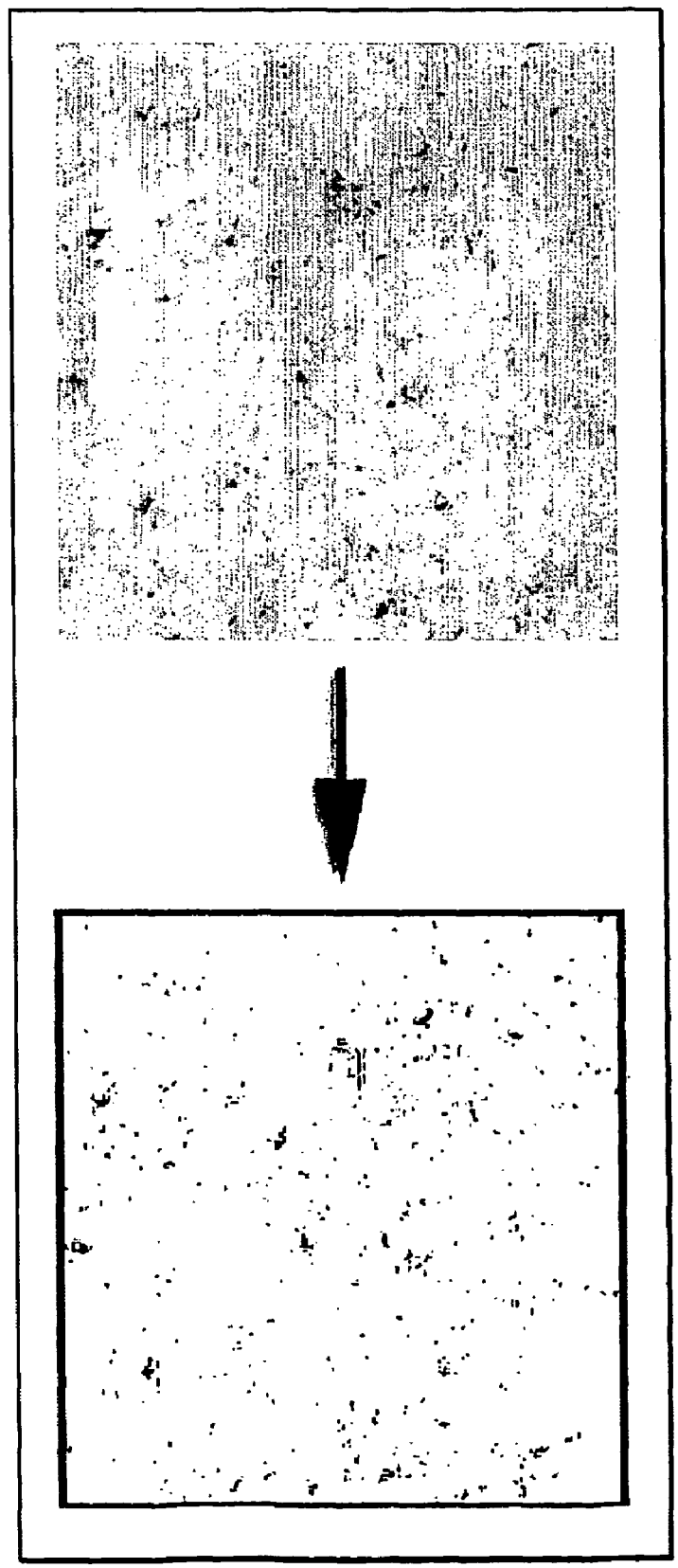
FIG. 6 is a representative digital image converted to its black and white counterpart image.

FIG. 6 shows the conversion of a representative image obtained in the cleansing assay to its black and white counterpart for subsequent percent coverage calculation. The Matlab technical computing software was used to segment the original image into 16 equally sized regions. The resultant images are first converted to Gray scale, then a threshold algorithm is performed on the Gray scale images to distinguish between the soiling material and endogenous topographical features of the skin. This process generates the black and white image.

To determine the minimum concentration of test surfactant needed to maximally detach vernix, an evenly applied 12-mil coating (21 mg/cm$^2$) of vernix was spread onto a set of circular Gortex™ membranes (1.9 cm$^2$) using an Accu-gate spreader. The coated membranes were gently rocked at 37° C. in 12 ml of either double-distilled water (blank) or a solution of sodium lauryl sulfate (SLS) diluted to 0.1%$^{w/v}$, 0.5%$^{w/v}$, or 1.0%$^{w/v}$. SLS is a surfactant commonly used to empirically model surfactant/skin interactions and is used in some skin cleansing formulations. After 18 hours, the turbidity of the SLS solutions was analyzed spectrophotometrically at 650 nm to assess the amount of vernix detachment. The results are shown in FIG. 7A.

In a separate experiment, surfactant-induced detachment of vernix from the skin surface was assessed. Vernix was applied to human cadaver skin, with film thicknesses ranging from 2 to 16 mg/cm$^2$. The treated skin sections were mounted in Franz diffusion cells and exposed to 0.5% $^{w/v}$/SLS. Following 24 hours of SLS exposure, flocculation of vernix was spectrophotometrically measured as solution turbidity at 650 nm. The results are shown in FIG. 7B.

Figure 7A:
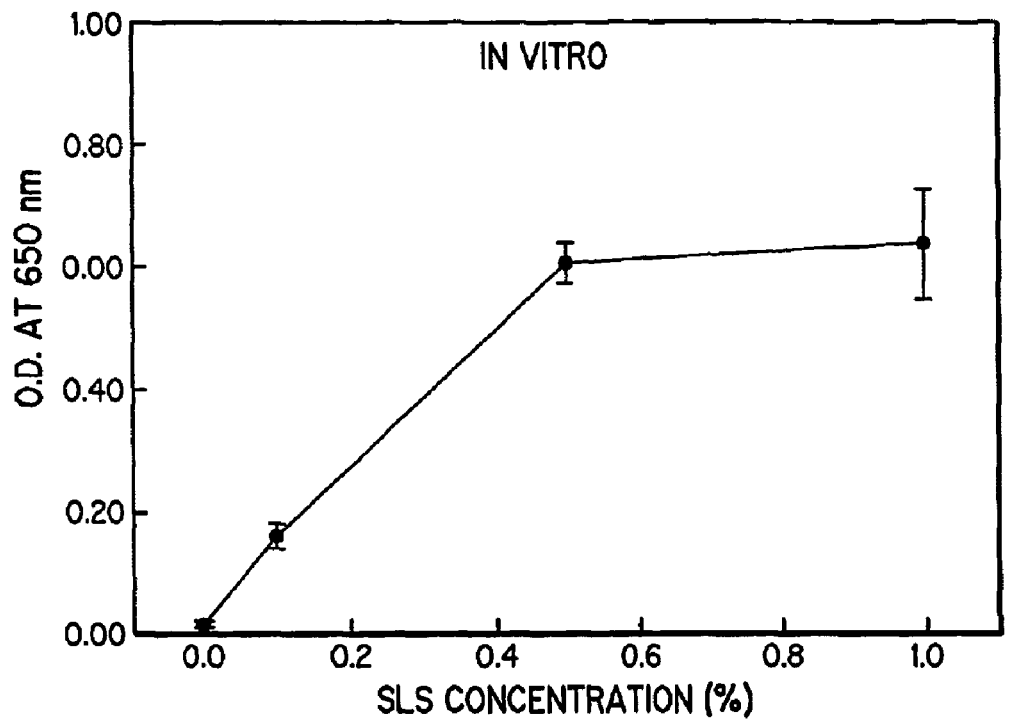
FIG. 7A is a graph showing vernix detachment in the presence of surfactant from an in vitro surface.
Figure 7B:
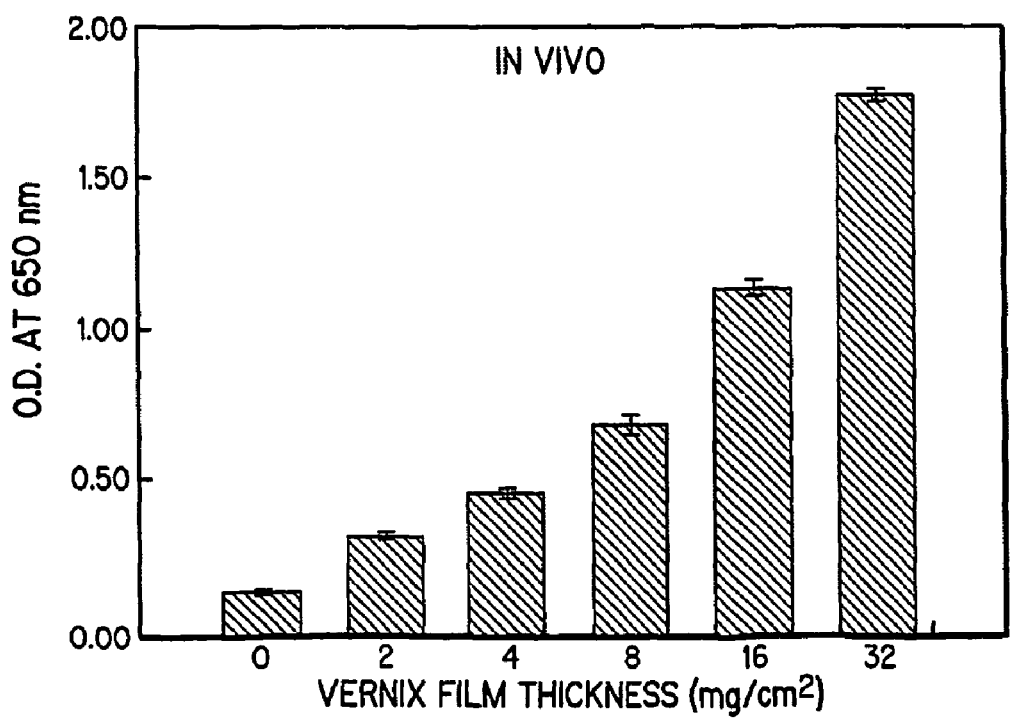
FIG. 7B is a histogram showing vernix detachment in the presence of surfactant from an in vivo surface treated with increasing thickness of a vernix film.

As shown in FIG. 7A, a concentration of about 0.5% $^{w/v}$ SLS achieved substantially maximum vernix detachment. Concentrations of SLS up to about 0.5% $^{w/v}$ demonstrated increasing vernix detachment. Concentration of SLS greater than about 0.5% $^{w/v}$ demonstrated only minimally increasing vernix detachment. As shown in FIG. 7B, in the presence of 0.5% $^{w/v}$ SLS, quantitatively more vernix was removed with surfactant when thicker vernix films were used. This dose-dependent increase in detachment of vernix from either Gortex™ or human cadaver skin following SLS exposure indicated that commonly used cleansing surfactants remove vernix from the newborn during the first bath.

The data demonstrated that all cleansing agents, including vernix, removed soil from the skin surface, as measured by a significant increase in the L-value using whole image analysis. Results among the cleansing agents were statistically indistinguishable. Analysis of magnified digital images indicated that vernix had better cleansing ability in deep pores, demonstrated by a significant reduction in the number of carbon particles at these sites. The data also demonstrated a dose dependent increase in turbidity at 600 nm following SLS exposure (p<0.05), indicating increasing detachment of vernix. No increase in turbidity was observed in control samples or in skin samples covered with equivalent amounts of petrolatum.

Among the clinical implications of the invention are the in vitro use of vernix as a skin cleansing material. Prenatally, vernix detaches into the amniotic fluid under the influence of pulmonary surfactant. This biological process is similar to self-cleaning (desquamation) of the stratum corneum. Vernix as an endogenous cleanser utilizes this cleansing function for optimal delivery room management during transition of the neonate, either full term or pre-term, to a nonsterile environment. The hydrophilic component of vernix aids in removing hydrophilic soils. The hydrophobic component of vernix aids in removing hydrophobic soils. The choice of an exogenous cleanser for the first bath may be tailored to detach soil and endogenous vernix, with vernix detachment either partial or complete as desired.

In one embodiment, vernix is removed from a newborn, collected, and stored at 4° C. The isolated vernix is thereafter used when cleansing the skin of the newborn from whom the vernix was obtained, and/or the mother of the newborn from whom the vernix was obtained. This may be continued for any cleansing procedure until the newborn and mother leave the hospital, or may be used for cleansing particular skin surfaces, either intact or compromised, or may be used until the isolated vernix is depleted.

In another embodiment, vernix is removed from a newborn. The isolated vernix is treated to render it physiologically compatible so that it may be applied to the skin of a different individual, that is, not the newborn from whom it was obtained or the mother of the newborn from whom it was obtained. The treatment is sufficient so that pathogens such as the human immunodeficiency virus, the hepatitis C virus, etc., and/or substances which may harbor pathogens such as blood, meconium, etc., are inactivated, killed, removed, etc. For example, vernix may be collected in a tube, covered, and treated by heat sterilization in an autoclave, by radiation exposure (light, x-rays, etc), or by other methods known to one skilled in the art. As further verification of the physiological compatibility of the isolated vernix, serological/immunological profiling may be performed on the newborn from whom vernix was isolated and mother. The isolated physiologically compatible vernix is then available for use to cleanse a skin surface of any individual, such as an individual whose skin is compromised, fragile, easily irritated, etc.

Other variations or embodiments of the invention will also be apparent to one of ordinary skill in the art from the above description. For example, a simulated cell component may be used as a vehicle to deliver surfactant protein to the skin surface to provide an anti-infective benefit, and also as a vehicle to deliver anti-oxidants such as Vitamin E to the skin. The composition may include other skin cleaning agents, and or other components such as emollients, humectants, etc. Thus, the forgoing embodiments are not to be construed as limiting the scope of this invention.

What is claimed is:

1. A physiologically compatible composition consisting of a plurality of hydrated synthetic cells in an effective amount to provide water in an effective concentration of about 65% to about 85% of the total composition to a skin surface, the hydrated synthetic cells dispersed in a lipid matrix in an effective amount to provide a minimum surface free energy of about 20 dynes/cm to the skin surface;
   wherein at least one lipid component of the lipid matrix is selected from the group consisting of cholesterol esters in a range of about 20% to about 35% of the lipid matrix, ceramides in a range of about 10% to about 20% of the lipid matrix, triglycerides in a range of about 10% to about 20% of the lipid matrix, cholesterol in a range of about 5% to about 10% of the lipid matrix, free fatty acids in a range of about 5% to about 10% of the lipid matrix, phospholipids in a range of about 5% to about 10% of the lipid matrix, wax esters in a range of about 2% to about 8% of the lipid matrix, squalene in a range of about 0.5% to about 5% of the lipid matrix, wax diesters in a range of about 0.5% to about 6% of the lipid matrix, and cholesterol sulfate in a range of about 0.1% to about 3% of the lipid matrix, the concentration of the at least one lipid component providing from about 5% to about 30% of lipid in the composition.

2. The composition of claim 1 capable of removing soiling material from a soiled skin surface.

3. The composition of claim 1 wherein the synthetic cells are selected from the group consisting of cubosomes, phospholipid liposomes, non-phospholipid liposomes, polymersomes, nanoparticles, microparticles, colloidosomes, and combinations thereof.

4. The composition of claim 1 providing a hydration profile of native vernix comprising a property selected from the group consisting of transporting water vapor, regulating a rate of water vapor loss, and combinations thereof.

5. A physiologically compatible composition consisting of a plurality of hydrated synthetic cells in an effective amount to provide water in an effective concentration of about 65% to about 85% of the total composition to a skin surface, the hydrated synthetic cells dispersed in a lipid matrix in an effective amount to provide a critical surface tension in a range of about 38 dynes/cm to about 41 dynes/cm to the skin surface; wherein at least one lipid component of the lipid matrix is selected from the group consisting of cholesterol esters in a range of about 20% to about 35% of the lipid matrix, ceramides in a range of about 10% to about 20% of the lipid matrix, triglycerides in a range of about 10% to about 20% of the lipid matrix, cholesterol in a range of about 5% to about 10% of the lipid matrix, free fatty acids in a range of about 5% to about 10% of the lipid matrix, phospholipids in a range of about 5% to about 10% of the lipid matrix, wax esters in a range of about 2% to about 8% of the lipid matrix, squalene in a range of about 0.5% to about 5% of the lipid matrix, wax diesters in a range of about 0.5% to about 6% of the lipid matrix, and cholesterol sulfate in a range of about 0.1% to about 3% of the lipid matrix, the concentration of the at least one lipid component providing from about 5% to about 30% of lipid in the composition.

6. A physiologically compatible composition consisting of a plurality of hydrated synthetic cells in an effective amount to provide water in an effective concentration of about 65% to about 85% of the total composition to a skin surface, the hydrated synthetic cells dispersed in a lipid matrix in an effective amount to provide a critical surface tension to the skin surface greater than 36 dynes/cm; wherein at least one lipid component of the lipid matrix is selected from the group consisting of cholesterol esters in a range of about 20% to about 35% of the lipid matrix, ceramides in a range of about 10% to about 20% of the lipid matrix, triglycerides in a range of about 10% to about 20% of the lipid matrix, cholesterol in a range of about 5% to about 10% of the lipid matrix, free fatty acids in a range of about 5% to about 10% of the lipid matrix, phospholipids in a range of about 5% to about 10% of the lipid matrix, wax esters in a range of about 2% to about 8% of the lipid matrix, squalene in a range of about 0.5% to about 5% of the lipid matrix, wax diesters in a range of about 0.5% to about 6% of the lipid matrix, and cholesterol sulfate in a range of about 0.1% to about 3% of the lipid matrix, the concentration of the at least one lipid component providing from about 5% to about 30% of lipid in the composition.

7. A physiologically acceptable composition consisting of a plurality of hydrated cubosomes in an effective amount to provide water in an effective concentration of about 65% to about 85% of the total composition to a skin surface, the hydrated cubosomes dispersed in a lipid matrix in an effective amount to provide to the skin surface a hydration profile of native vernix comprising a property selected from the group consisting of transporting water vapor, regulating a rate of water vapor loss, and combinations thereof; wherein at least one lipid component of the lipid matrix is selected from the group consisting of cholesterol in a range of about 5% to about 10% of the lipid matrix, cholesterol esters in a range of about 20% to about 35% of the lipid matrix, ceramides in a range of about 10% to about 20% of the lipid matrix, triglycerides in a range of about 10% to about 20% of the lipid matrix, free fatty acids in a range of about 5% to about 10%, phospholipids in a range of about 5% to about 10%, wax esters in a range of about 2% to about 8% of the lipid matrix, wax diesters in a range of about 0.5% to about 6% of the lipid matrix, squalene in a range of about 0.5% to about 5% of the lipid matrix, and cholesterol sulfate in a range of about 0.1% to about 3% of the lipid matrix, the concentration of the at least one lipid component providing from about 5% to about 30% of lipid in the composition.

8. A physiologically compatible composition consisting of a plurality of hydrated synthetic cells in an effective amount to provide water in an effective concentration of about 65% to about 85% of the total composition to a skin surface, the hydrated synthetic cells dispersed in a lipid matrix in an effective amount to effect barrier repair to a skin surface as a semi permeable film wherein at least one lipid component of the lipid matrix is selected from the group consisting of cholesterol esters in a range of about 20% to about 35% of the lipid matrix, ceramides in a range of about 10% to about 20% of the lipid matrix, triglycerides in a range of about 10% to about 20% of the lipid matrix, cholesterol in a range of about 5% to about 10% of the lipid matrix, free fatty acids in a range of about 5% to about 10% of the lipid matrix, phospholipids in a range of about 5% to about 10% of the lipid matrix, wax esters in a range of about 2% to about 8% of the lipid matrix, squalene in a range of about 0.5% to about 5% of the lipid matrix, wax diesters in a range of about 0.5% to about 6% of the lipid matrix, and cholesterol sulfate in a range of about 0.1% to about 3% of the lipid matrix, the concentration of the at least one lipid component providing from about 5% to about 30% of lipid in the composition.

9. A composition consisting of vernix in a form selected from the group consisting of natural vernix, synthetic vernix, and vernix comprising a plurality of hydrated synthetic cells dispersed in a lipid matrix, wherein at least one lipid component of the lipid matrix is selected from the group consisting of cholesterol esters in a range of about 20% to about 35% of the lipid matrix, ceramides in a range of about 10% to about 20% of the lipid matrix, triglycerides in a range of about 10% to about 20% of the lipid matrix, cholesterol in a range of about 5% to about 10% of the lipid matrix, free fatty acids in a range of about 5% to about 10% of the lipid matrix, phospholipids in a range of about 5% to about 10% of the lipid matrix, wax esters in a range of about 2% to about 8% of the lipid matrix, squalene in a range of about 0.5% to about 5% of the lipid matrix, wax diesters in a range of about 0.5% to about 6% of the lipid matrix, and cholesterol sulfate in a range of about 0.1% to about 3% of the lipid matrix, the concentration of the at least one lipid component providing from about 5% to about 30% of lipid in the composition; and an emulsifier in a biocompatible cleansing carrier formulation.

10. The composition of claim 9 wherein the emulsifier is selected from the group consisting of a soap, a surfactant, and combinations thereof.

11. The composition of claim 9 in a formulation selected from the group consisting of a liquid, a solid, a gel, a cream, and a lotion.

* * * * *